United States Patent [19]
Shah et al.

[11] Patent Number: 6,039,975
[45] Date of Patent: Mar. 21, 2000

[54] COLON TARGETED DELIVERY SYSTEM

[75] Inventors: Navnit Hargovindas Shah; Aruna M. Railkar, both of Clifton; Wantanee Phuapradit, Jersey City, all of N.J.

[73] Assignee: Hoffman-La Roche Inc., Nutley, N.J.

[21] Appl. No.: 08/717,032

[22] Filed: Sep. 20, 1996

Related U.S. Application Data

[60] Provisional application No. 60/005,704, Oct. 17, 1995.

[51] Int. Cl.⁷ ....................................................... A61K 9/24
[52] U.S. Cl. ........................................... 424/473; 424/472
[58] Field of Search ...................................... 424/472, 473

[56] References Cited

U.S. PATENT DOCUMENTS

| | | | |
|---|---|---|---|
| 4,609,374 | 9/1986 | Ayer | 424/473 |
| 4,668,517 | 5/1987 | Weber et al. | |
| 4,871,549 | 10/1989 | Ueda et al. | |
| 4,891,223 | 1/1990 | Ambegaonkar et al. | 424/473 |
| 5,171,580 | 12/1992 | Iamartino et al. | |
| 5,225,202 | 7/1993 | Hodges et al. | |

FOREIGN PATENT DOCUMENTS

| | | | |
|---|---|---|---|
| 0148811 | 7/1985 | European Pat. Off. | 424/473 |
| 1804736 | 6/1969 | Germany | 424/472 |

OTHER PUBLICATIONS

W. Phuapradit, et al, In Vitro Characterization Of Polymeric Membrane Used For Controlled Release Application, Drug Development and Industrial Pharmacy, vol. 21(8) pp. 955–963 (1995).

S.S. Rao, et al, Development And In Vitro/In Vivo Evaluation Of A Colonic Release Capsule Of Vasopressin, International Journal Of Pharmaceutics, vol. 86 pp. 35–41 (1992).

D. Friend, et al, A Colon–Specific Drug–Delivery System Based On Drug Glycosides And The Glycosidases Of Colonic Bacteria, J. Med. Chem. vol. 27 pp. 261–266 (1984).

C. Larsen, et al, Macromolecular Prodrugs. XVI. Colon–Targeted Delivery–Comparison Of The Rate Of Release Of Naproxen From Dextran Ester Prodrugs In Homogenates Of Various Segments Of The Pig Gastrointestinal (GI) Tract, Pharmaceutical Research, vol. 6, No. 12 pp. 995–999 (1989).

M.J. Dew, et al, An Oral Preparation To Release Drugs In The Human Colon, British Journal of Clinical Pharmacology, vol. 14 pp. 405–408 (1982).

J.G. Hardy, et al, Drug Delivery To the Proximal Colon, J. Pharm. Pharmacol, vol. 37 pp. 874–877 (1985).

*Primary Examiner*—Peter F. Kulkosky
*Attorney, Agent, or Firm*—George W. Johnston; William H. Epstein; Briana C. Buchholz

[57] ABSTRACT

A novel delivery system for targeting drugs to the colon is herein described. The system is a tablet comprised of three parts: 1) an outer enteric coating, 2) an inner semi-permeable polymer membrane containing a plasticizer and 3) a central core comprising swelling excipients and an active ingredient. The novel dosage form described herein will release the drug consistently in the colon by a time-dependent explosion mechanism.

This delivery system is particularly suitable for delivering viral protease inhibitors to the colon.

14 Claims, 4 Drawing Sheets

COLON TARGETED DELIVERY SYSTEM

This application claims the benefit of U.S. Provisional Ser. No. 60/005,704, filed Oct. 17, 1995.

FIELD OF THE INVENTION

This invention relates to an oral delivery system for delivering a precise amount of a pharmaceutical product to the colon without premature delivery of the product to the upper gastrointestinal (GI) tract. More specifically, this invention relates to an oral delivery system that operates by a time-dependent explosion mechanism.

BACKGROUND DESCRIPTION

An oral delivery system that can precisely target drugs to the colon without prematurely delivering drugs to the upper GI tract is important and advantageous in a number of ways. Such a delivery system can be used to more effectively treat local bowel disease such as ulcerative colitis, because it minimizes systemic absorption through the upper GI tract and by so doing, maximizes the amount of drug delivered to the colon. Also, by using such delivery system, enema dosage forms, which are often impractical, and are ineffective for delivering drug to the ascending colon, may be avoided.

For drugs that are absorbed through the colon, e.g., proteins and peptide drugs, such delivery system can be used to maximize overall systemic absorption of these drugs. By avoiding exposure of the protein or peptide drugs to the upper GI tract, intraluminal degradation and breakdown of the drug can be eliminated to a large extent. Furthermore, the longer transit time for drugs in the colon (17–24 hrs) compared to the small intestine (3–4 hrs) will tend to improve overall systemic absorption of these protein or peptide drugs (1).

Oral delivery systems designed to deliver drugs to the colon are known. Dew et al (2) introduced the concept of enteric coating to target the drugs to the colon. Dew et al. reported use of an acrylic based resin (Eudragit-S®, Röhm Pharm. Co., Ltd) to coat 5-amino salicylic acid or steroids as a means to deliver these drugs to the colon. Eudragit-S®, a widely used enteric coating to produce acid resistant formulations, proved to be reasonably effective in achieving release of drug in the ascending colon when used at a thickness of 95–135 µm. However, Eudragit S® dissolves above pH 7.0. Since the small intestinal pH is variable and can occasionally exceed pH 7.0, enteric coating alone can lead to premature dissolution of the drug in the small intestine and therefore does not provide a predictable and precise colon-targeted delivery system.

Saffran et al (3) reported the use of azopolymers (i.e. polymers cross-linked with azo-aromatic groups) for colonic delivery. These are degraded by colonic bacterial azoreductase activity but are unaffected by gastric enzymes, and therefore were proposed as potential coatings for colonic delivery systems. These coatings are not ideal for a colon targeted delivery system, since release of drug depends on the presence of colonic anaerobic bacteria. Since the flora of anaerobic bacteria in the colon is variable, these polymers provide inconsistent drug delivery to the colon. Also, the safety of these polymeric coating materials is not completely established.

An oral delivery system based on a time-controlled explosion mechanism is described by Ueda et al., U.S. Pat. No. 4,871,549. The formulations described by Ueda et al represent a core of active ingredient and swelling agents encased by a single insoluble membrane. When this formulation is exposed to gastrointestinal fluid, the core swells and eventually bursts the encasing membrane. Ueda's system is not ideal for use as a colon-targeted delivery system since the swelling of the core begins as soon as the formulation reaches the stomach. Hence, variation in transit time through stomach will alter the site of drug delivery. Ueda discloses that the release profile of drug depends upon the properties of the core; that is, the type and amount of swelling agents, the ratio of drug to swelling agent, and whether the drug and swelling agent is layered or combined together. The release of drug using Ueda's system is not disclosed as being dependent on the composition or functional properties of the encasing insoluble membrane. In addition, Ueda, et al does not disclose any particular membrane that would burst consistently after 4–6 hours intestinal transit time or would provide for a consistent delivery of drug to the colon.

A delivery system for specifically targeting the colon is described by lamartino et al in U.S. Pat. No. 5,171,580 (5). This delivery system consists of a core of active ingredient surrounded by three layers: an outer enteric coating, a middle gelling polymer layer which swells when exposed to the enteric juice, and an anionic copolymer inner layer which is soluble at a pH above 7.0. The outer enteric coat is designed to readily dissolve upon reaching the small intestine. The middle polymer layer is designed to swell and form a protective layer for the inner anionic layer and core for about 2–4 hours while the layered dosage form transits the small intestine. After 2–4 hours, the protective layer disintegrates followed by complete disintegration of the inner anionic layer. Subsequently, there is dissolution of the core and release of active ingredient at about the time the formulation reaches the colon.

Iamartino's system has a number of disadvantages for use as a colon-targeted delivery system. First, the high viscosity grade polymer used as the middle gelling polymer layer may cause cracking or breakdown of the outer enteric coating, resulting in leakage of gastric fluid through the enteric coating and premature dissolution of drug in the small intestine. This system also provides for variable and imprecise drug delivery to the colon due to the variable lag time associated with swelling of the polymer, and disintegration of the inner anionic coating. Under these circumstances it is possible for the tablet to reach the colon prior to complete dissolution of the polymer thus diminishing exposure of the drug to the colonic environment.

A system is proposed in this invention which combines a time-dependent explosion approach and enteric coating to achieve precise and predictable delivery of drug only to the colon. This precision and predictability is in part achieved by selecting a combination of an acid resistant semi-permeable membrane of a polymer containing a plasticizer and a swellable core which will cause the membrane to burst consistently after 4–6 hours exposure to small intestinal fluid.

SUMMARY OF THE INVENTION

A delivery system for targeting drugs to the colon is herein described. The drug delivery system of this invention is a tablet comprising three parts: 1) an outer enteric coating; 2) an inner semi-permeable polymer membrane containing a plasticizer; and 3) a central core comprising a swelling agent(s) and an active ingredient. The three parts of this system function to provide for release of drug to the colon without premature delivery of drug to the upper GI tract. The outer enteric coat, being resistant to the acidic gastric environment, keeps the tablet intact until the tablet reaches the small intestine. Once in the small intestine, the outer enteric coating dissolves allowing for gastrointestinal fluid to diffuse through the semi-permeable membrane into the core. No drug is released at this time. The core swells as a result of pentration of gastrointestinal fluid during the transit of the tablet through the small intestine. Finally, after a consistent period of 4–6 hours transit in the small intestine, the swollen core bursts the semi-permeable membrane releasing active ingredient in the colon.

The inventive dosage form will release the drug consistently in the colon in a precise and predictable manner. The precision and predictability is attributable to the functional properties of the membrane, in particular, percent elongation of the membrane (from about 2.0 to about 3.5%). A membrane having a percent elongation between about 2.0 and 3.5 will allow for the explosion of the semi- permeable membrane and release of active ingredient 4–6 hours after the tablet first enters the small intestine. Since small intestinal transit time is consistently 4–6 hours, release of active ingredient occurs when the tablet enters the colon. This percent elongation of the membrane is achieved using a polymer containing a plasticizer from about 10 to about 30% w/w of the membrane.

Because this system combines the use of an outer enteric coat resistant to gastric juices and a semi-permeable membrane designed to burst 4–6 hours transit time in the small intestine, the site of drug delivery (i.e. the colon) is not influenced by individual differences in gastric emptying time, differences in solubility of active drug in the core, pH of the intestinal tract or presence of anaerobic bacteria in the colon.

The inventive targeted delivery system is particularly suitable for colonic delivery of protease inhibitors, as agents useful in combating viral infections, such as retroviruses, and more specifically HIV virus.

BRIEF DESCRIPTION OF DRAWINGS

Preferred-embodiments of the invention are described below with reference to the drawings wherein.

DETAILED DESCRIPTION OF THE INVENTION

The colon-targeted delivery system of the invention is comprised of a tablet having three components:

(A) a core of active ingredient(s) and swelling agent(s);

(B) an inner semi-permeable membrane; and (C) an outer enteric coating.

Figure 1:
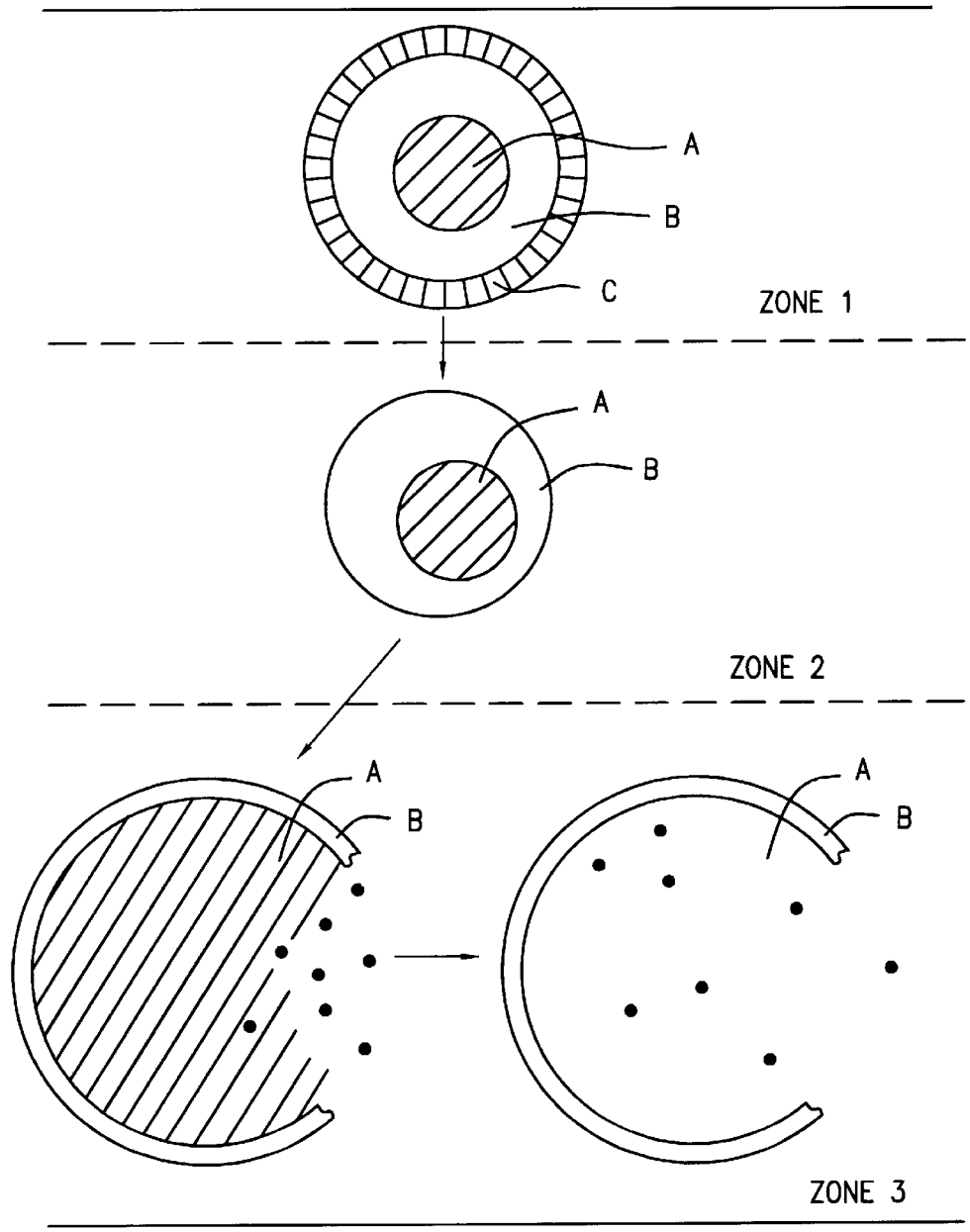
FIG. 1 is a Schematic of Colon-Targeted Delivery System including its composition and its dissolution and explosion over time.

A schematic of these three components of this colon targeted delivery system is shown at the top of FIG. 1. In FIG. 1, (A) represents the core, (B) represents the semi-permeable membrane, and (C) represents the outer enteric coating. The composition of each of these three components of the delivery system of the invention are next described.

1) Core:

The core contains an active ingredient(s) in a pharmaceutical acceptable carrier mixed with a swelling agent(s) and various other pharmaceutically acceptable excipients, such as binders, lubricants or diluents.

Any conventional pharmaceutically acceptable swelling agent may be used in the core. The swelling agent may be a disintegrating agent, e.g. croscarmellose sodium (Ac-Di-Sol®, FMC Corp., Philadelphia Pa.), modified starch, sodium starch glycolate, or sodium carboxymethyl cellulose; synthesized polymers, e.g. cross-linked polyvinyl pyrrolidone, polyvinyl acetate, polyacrylic acid, or an ion exchange resin (Amberlite IRP-88®, Röhm Pharm, Co. Ltd.); osmotic agents, e.g. mannitol, sucrose, glucose; and the like and combinations thereof. The preferred swelling agent is a combination of croscarmellose sodium and mannitol.

It is preferable that the swelling agent or combination of swelling agents represents about 5–50% by weight of the core, more preferably about 10–30%. When an osmotic agent, such as mannitol, is used in combination with another swelling agent, the amount of osmotic agent is preferably about 10–40% by weight of the core, more preferably about 15–25%. When the osmotic agent is mannitol and this osmotic agent is used in combination with a disintegrating agent, such as croscarmellose sodium it is preferable to use the disintegrating agent and mannitol in a weight ratio of about 1:2 to 1:4, respectively.

Any conventional pharmaceutically acceptable binder, lubricant or diluent may be used in the formulation of the core. The preferred binder is polyvinyl pyrrolidone. The preferred lubricant is magnesium stearate. The preferred diluent is microcrystalline cellulose (Avicel PH 102®, FMC Corp., Philadelphia. Pa.).

2) Semi-Permeable Membrane:

The membrane coating of the invention is a semi-permeable polymer membrane. This semi-permeable membrane allows water influx but prevents outward diffusion of drug. Any polymer material having such properties may be used in accordance with the invention, such as ethyl cellulose, cellulose acetate, cellulose triacetate, cellulose tributyrate, polyvinyl chloride, etc. The preferred polymer material is ethyl cellulose.

Figure 2:
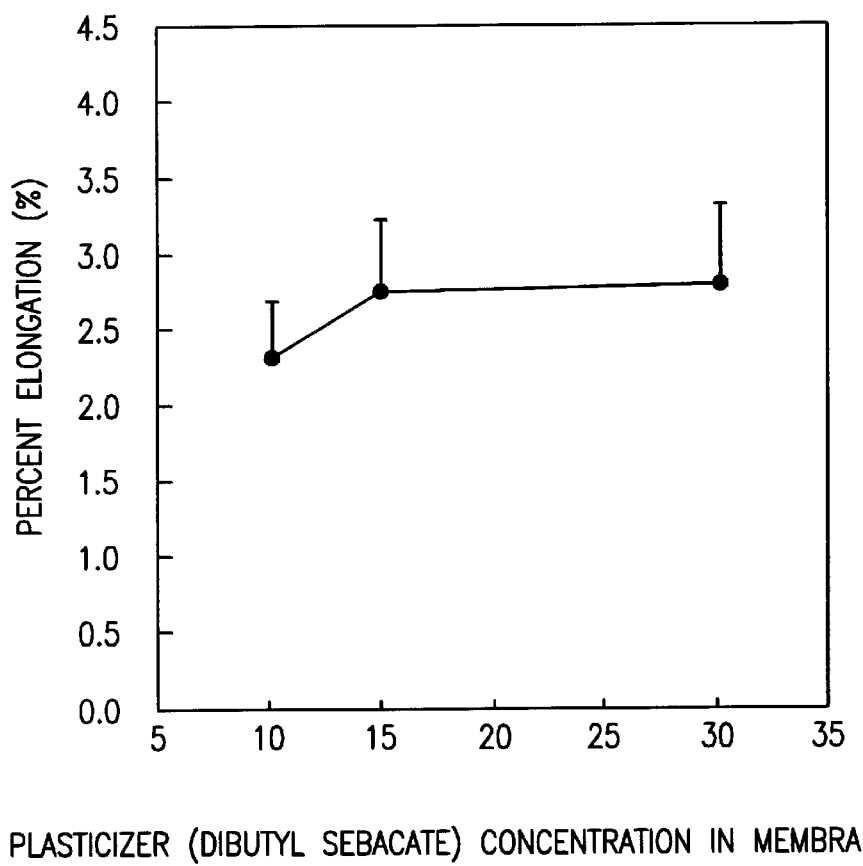
FIG. 2 is a graphic presentation of the relationship between concentration of plasticizer in a membrane and the percent elongation of that membrane.

The polymer material is mixed with a plasticizer such that the plasticizer represents from about 10 to about 30% w/w of the membrane, preferably about 15% w/w of the membrane. This amount of plasticizer allows the membrane to have a percent elongation of from about 2.0 to about 3.5%, which percent elongation allows the membrane to burst consistently after 4–6 hours exposure to intestinal fluid. Percent elongation represents the ductility of the membrane and is a measure of the strain or increase in length upon the stress. In general, the higher the concentration or amount of plasticizer used in the membrane, the higher the percent elongation of the polymer membrane. This relationship between amount of plasticizer and percent elongation is depicted graphically in FIG. 2, where the x-axis represents concentration of plasticizer in the membrane and the y-axis represents percent elongation of the membrane For purposes of FIG. 2, the plasticizer is dibutyl sebecate and the membrane is ethylcellulose in combination with dibutyl sebecate. As depicted in FIG. 2, when 10–30% plasticizer is used, the percent elongation of the membrane ranges between about 2.0 and 3.5%. When less than 10% plasticizer is used, the percent elongation of the membrane is lowered to the point that the polymer membrane will break (or explode) prior to 4–6 hours exposure to intestinal fluid. When plasticizer is used in excess of 30%, the percent elongation increases to the point that the membrane of the delivery system will not break but rather continue to stretch during its passage through the colon.

In accordance with this invention, any conventional plasticizer may be used in the semi-permeable membrane, such as dibutyl sebacate, acetylated monoglycerides, dibutyl phthalate, diethyl phthalate, medium chain triglycerides etc. The preferred plasticizer is dibutyl sebacate. When any such plasticizer is used in the membrane at an amount from 10 to 30% w/w of the membrane, the semi-permeable membrane will have a percent elongation about 2.0 to 3.5%.

The weight of membrane coating applied to the core is not critical, and preferably about 10–30% by weight of the core, more preferably about 15–20%, most preferably, about 17.5%. The thickness of the membrane is not critical but is preferably from about 50 to about 400 $\mu$m. Correlated with percent elongation is tensile strength and elasticity of the membrane. Tensile strength is defined as the applied load per unit cross-sectional area of a membrane and represents the strength of the membrane. Elasticity is a measure of the hardness of the membrane. The tensile strength of the semi-permeable membrane having the above mentioned composition of polymer and 10–30% plasticizer and having a percent elongation from about 2.0 to about 3.5% is from about 1000–3500 psi. The modulus of elasticity of such membrane is from about 95 to about 150 ksi.

The tensile strength (psi), percent elongation (%) and elasticity of the membrane (ksi) are properties which can be determined by methods known in the art. These properties can be measured using an Instron Series IX materials testing software by the procedures outlined in Phuapradit, W. et al. (6).

3) Outer enteric coating.

Any conventional acid-resistant enteric coating materials may be used in the delivery system of the invention. Examples of enteric coatings are aquateric materials, such as hydroxypropyl methylcellulose phthalate, polyvinyl acetate phthalate, methacrylic acid, methylmethacrylate, or combinations thereof. Preferred is a methacrylic acid/methyl methacrylate copolymer having a ratio of free carboxyl groups to the ester groups of about 1:1, and which dissolves in media at and above pH 6 (e.g., Eudragit L100®, Röhm Pharma Co.), or hydroxypropyl methylcellulose phthalates which dissolves in media at and above pH 5.5 (e.g., HP-55®, Eastman Chemical Co.; ). The percent content range (by weight) of methoxy groups, hydroxypropoxy groups and carboxybenzoyl groups in the preferred hydroxypropyl methycellulose phthalate for use in the invention is 18–22%, 4–9%, and 27–35%, respectively.

The enteric coating materials are preferably formulated with appropriate plasticizers, such as distilled acetylated monoglycerides or triethyl citrate. Any conventional plasticizer such as those enumerated above for the semi-permeable membrane may be used. However, the preferred plasticizer for use in the outer enteric coating is a distilled acetylated monoglyceride derived from partially hydrogenated soybean oil which has been fully ($\geq$96%) acetylated (e.g., Myvacet 9–45®, Eastman Chemical Co.). The amount of plasticizer used in the enteric coating is not critical, but preferably represents about 5–25% w/w of the enteric coating.

In accordance with this invention, the enteric coating comprises preferably 5–25% by weight of the core, more preferably 15%. The thickness of the enteric coating is not critical but should be from about 50 $\mu$m to about 350 $\mu$m, preferably 100 $\mu$m. The coating weight and thickness will depend on the degree of acid resistance of the enteric coating material used and can be determined by one skilled in the art.

Next is described the method of making this drug delivery system.

The core of the delivery system is prepared by any conventional means. Preferably, the core is prepared by wet granulation. Using an F-press, the granulation is compressed into tablets by conventional means.

The semi-permeable membrane may be applied to the core using any conventional coating system. Preferably it is applied using a suitable air spray system using about 8% w/w ethycellulose solution in a mixture of methylene chloride and absolute alcohol (6:4 v/v) or other suitable solvent.

The enteric coatings may be applied to the core encased by the semi-permeable membrane by any conventional means for example, by using a suitable air spray system.

Next is described the function of each component of this drug delivery system. FIG. 1 is a schematic showing how the 3 components operate in the stomach, small intestine and colon. In the stomach (depicted as Zone 1 in FIG. 1), the delivery system has three intact components: the core (A), the semi-permeable membrane encasing the core (B), and the outer enteric coat (C). The outer enteric coat is stable in acid conditions, and remains intact in the stomach. Therefore, no release of active ingredient from the core occurs while the delivery system transits the stomach. Next, the dosage form is emptied into the small intestine (depicted as Zone 2), at which time the outer enteric coat dissolves thus exposing the semi-permeable polymeric membrane (B) to the small intestinal fluids. This membrane permits intestinal fluid to absorb into the core and swell the core but prevents any drug release at this time. Swelling of the core continues for 4–6 hours exposure to the intestinal fluid, at which time the delivery system enters the colon (Zone 3), the membrane burst, and the core is exposed to the colonic environment. The core containing the active ingredient(s) next disintegrates, and subsequently releases the active ingredient(s) into the colon. The core completely and readily disintegrates (in about 1–2 hours) releasing virtually all of the active ingredient(s) into the ascending colon.

The determination of the ability of the delivery system of this invention to deliver active ingredient to the colon and not prematurely to the upper GI tract may be performed by methods known in the art, such as the USP dissolution test procedure with the USP XXIII Paddle Method described in the U.S. Pharmacopacia. Alternatively, the release of active ingredient can be determined using the USP dissolution test procedure with the USP XXIII Basket Method. The Basket Method is described in the U.S. Pharmacopoeia (USP) XXIII & National Formulary (NF) XVII (The United States Pharmacopoeia Convention, Inc., Rockville, Md. 1990). The analysis is performed by a known UV spectrophotometric method.

The colon-targeted delivery system of this invention is particularly suitable for colonic delivery of proteinase inhibitors. As used herein, proteinase inhibitor refers to those compounds which inhibit aspartate proteases of viral origin which are useful in the prophylaxis or treatment of viral infections caused by retroviruses, such as Human Immunodificiency Virus (HIV), in both human and non-human mammals. Details of the design of such proteinase inhibitors can be found, for example, in Roberts, N. A. et al., (7); Overton, H. A., et al. (8); Tucker, T. J., et al. (9); and Phylip, L. H., et al (10).

Any proteinase inhibitor may be used as the active ingredient of this invention. As examples of the proteinase inhibitors which may be used as active ingredient in this delivery system include inhibitors described in U.S. Pat. No. 4,661,473, U.S. Pat. No. 5,196,438, U.S. Pat. No. 5,157,041, U.S. Pat. No. 5,192,668, European Pat. No. Publication 594 540-A1 published Apr. 27, 1994, European Pat. No. Publication 526 009-A1 published Feb. 3,1993, Ghosh, A. K., et al., J. Med. Chem. 36: 2300 (1993); Fässler A., et al, Biorg Med. Chem. Letters 3:2837 (1993) and the like.

EXAMPLES

The invention is illustrated by the following examples. These examples are illustrative only and do not limit the scope of the invention in any way.

Example 1

100 mg Coated Tablets
Core: 11/32" round standard concave tablet with a hardness of 10–15 scu.

|  | mg/tablet |
|---|---|
| 2-hydroxy-4-[5-(2,3-dihydroxyphenyl)-penlyloxy]-3-propyl benzoic acid (active ingredient) | 100.00 |
| Avicel PH 102 ® | 70.80 |
| Croscarmellose Sodium | 16.70 |
| Mannitol | 50.00 |
| Polyvinyl pyrrolidone | 10.00 |
| Magnesium Stearate | 2.50 |
| Semi-permeable Membrane Coating: (Thickness 210–220 um) |  |
| Ethylcellulose | 31.25 |
| Dibutyl Sebacate | 6.25 |
| Enteric Coating: |  |
| Eudragit L100 ® | 65.33 |
| Triethyl Citrate | 6.53 |
| Total Tablet Weight | 359.36 |

Example 2

60 mg Coated Tablets
Core: 9/32" round standard concave tablet with a hardness of 10–15 scu.

|  | mg/tablet |
|---|---|
| 5-Aminosalicylic Acid (active ingredient) | 60.00 |
| Avicel PH 102 ® | 37.50 |
| Croscarmellose Sodium | 15.00 |
| Mannitol | 30.00 |
| Polyvinyl pyrrolidone | 6.00 |
| Magnesium Stearate | 1.50 |
| Semi-permeable Membrane Coating: (Thickness 390–460 um) |  |
| Ethylcellulose | 18.70 |
| Dibutyl Sebacate | 3.30 |
| Enteric Coating: |  |
| HP55 ® | 35.15 |
| Myvacet 9–45 ® | 2.85 |
| Total Tablet Weight | 201.00 |

Example 3

Method of Preparation of Coated Tablets of Examples 1 & 2

The active ingredient of Examples 1 or 2 was mixed with the other stated excipients in the core of Examples 1 and 2, respectively. Each mixture was granulated, dried and tableted using an F-press by routine methodology. Next the ethyl cellulose was mixed with dibutyl sebacate and the resulting mixture placed into a 6:4 v/v solution of methylene chloride and ethyl alcohol. This solution was applied to the core tablet using an air spray system.

Next, the enteric coating materials as specified in Examples 1 and 2 respectively, were mixed and applied to the surface of the semi-permeable membrane using an air spray system.

Example 4

Release of the Active Ingredients from tablets in Examples 1 & 2

The release of the active ingredients from the dosage form of Examples 1 and 2 was determined according to the USP XXII paddle method utilizing a stirring speed of 50 rpm. The dissolution medium was used as specified (i.e., 0.1N HCl followed by phosphate buffer, pH 7.5). The analysis was performed by a UV spectrophotometric method.

Figure 3:
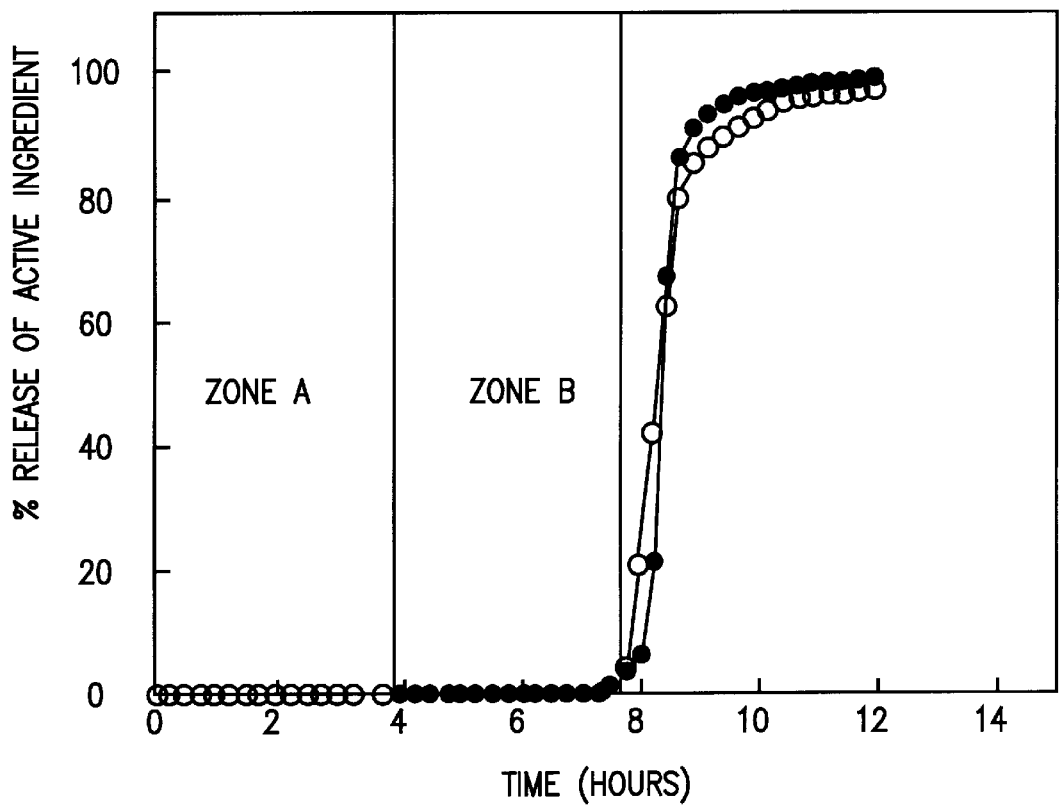
FIG. 3 is a Release Profile for the active ingredient of Example 1.

The release profile of the delivery system of Example 1 is shown graphically as FIG. 3. FIG. 3 shows the percent active ingredient released (y axis) over time in hours (x axis). For Example 1, two experiments were performed. In the first experiment (designated in FIG. 3 as open circles) the delivery system was exposed to 4 hours 0.1 N HCl (Time 0–4 on x-axis) followed by 8 hours exposure to phosphate buffer, pH 7.5 (Time 4–12 on x-asis). In the second experiment (designated in FIG. 3 as blackened circles), the delivery system was exposed only to 8 hours phosphate buffer, pH 7.5 (Time 4–12 hours on x-axis). In FIG. 3, Zone A from time 0–4 hours on the x-axis is the time the delivery system is exposed to 0.1N HCl, and simulates exposure of the delivery system to gastric fluid. Zone B, from time 4–12 hours on the x-axis is the time the delivery system is exposed to phosphate buffer and simulates exposure of the delivery system to intestinal fluid. In the first experiment, during the initial 4 hours exposure to acid medium (0.1 N HCl) and additional 4 hour exposure to phosphate buffer, pH 7.5, no active ingredient was released. Between 4 hours and 6 hours exposure to phosphate buffer; however, 100% of the active ingredient was released. In the second experiment, there was no release of active ingredient during the first 4 hours of the delivery system to phosphate buffer. However 100% release of active ingredient occurred from 4–6 hours after exposure to phosphate buffer.

Figure 4:
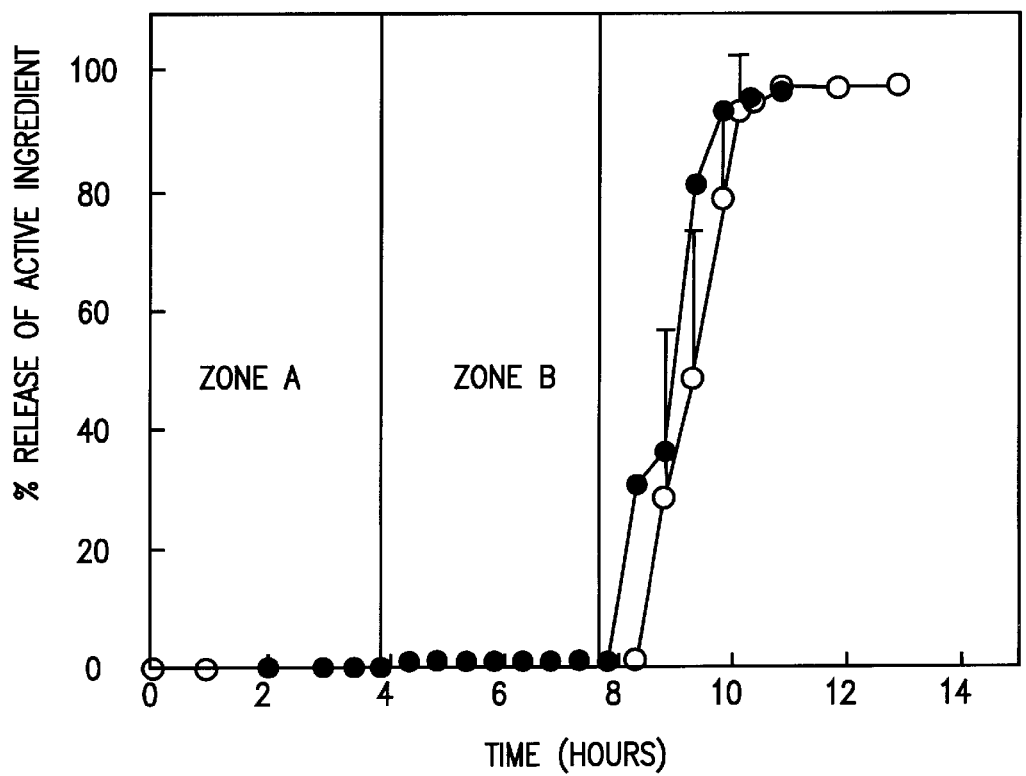
FIG. 4 is a Release Profile for the active ingredient of Example 2.

The release profile of the delivery system of Example 2 is shown graphically in FIG. 4. For purposes of this graph, the open circles designate a first experiment whereby the delivery system was exposed initially to a dissolution medium of 0.1 N HCl for 4 hours (Time 0–4 hours on x-axis) followed by 10 hours exposure to phosphate buffer, pH 7.5 (Time 4–14 hours on x-axis). The blackened circles designate a second experiment whereby the delivery system was exposed initially to 2 hours of 0.1 N HCl (Time 2–4 hours on x-axis) followed by 10 hours exposure to phosphate buffer, pH 7.5 (Time 4–14 hours on x-axis). In FIG. 4, Zone A (time 0–4 hours on x-axis) and Zone B (time 4–12 hours on x axis) simulates the time of exposure of the delivery system to gastric fluid or intestinal fluid, respectively. As seen from the graph of FIG. 4, there was no release of active ingredient during the initial 2 or 4 hour exposure to 0.1 N HCl in the first and second experiments, nor was there any release of active ingredient in the first and second experiments during the first 4 hour exposure of the delivery system to phosphate buffer pH 7.5. However, in both the first and second experiments, from 4–6 hours after exposure of the delivery system to phosphate buffer, pH 7.5, virtually 100% of active ingredient was released. This 100% release occurred regardless of whether the delivery system was initially exposed to 2 or 4 hours of 0.1 N HCl.

Taken together, FIGS. 3 and 4 demonstrate that 100% release of active ingredient occurs consistently between 4–6 hours after exposure of the delivery system to a dissolution medium of phosphate buffer pH 7.5 (i.e., 4–6 hours after exposure to small intestine) and this release occurs consistently regardless of the time of initial exposure to acid (i.e. transit time through stomach).

Example 5

| 150 mg Coated Tablets | |
|---|---|
| | mg/tablet |
| Core: | |
| N-tert.butyldecahydro-2-2(R)-hydroxy-4-phenyl-3(S)-N-2-quinolylcarbonyl-L-asparaginyl aminobutyl-4aS,8aS isoquinoline-3(S)-carboxamide (active ingredient) | 150.0 |
| Avicel PH 102 ® | 95.0 |
| Croscarmellose Sodium | 30.0 |
| Mannitol | 60.0 |
| Polyvinyl pyrrolidone | 12.0 |
| Magnesium stearate | 3.0 |
| Semi-permeable Membrane Coat: | |
| Ethylcellulose | 18.70 |
| Dibutyl sebacate | 7.5 |
| Enteric Coat: | |
| HP55 ® | 83.2 |
| Myvacet 9–45 ® | 6.8 |
| Total Tablet Weight | 490.0 |

Example 6
Method of Preparation of Tablet of Example 5

The active ingredient of Example 5 is mixed with the stated exicipients in the core and granulated. The granulation is dried and tabulated using an F-press by routine methodology.

Next the ethylcellulose is mixed with dibutyl sebacate and the mixture placed into a 6:4 v/v solution of methylene chloride and ethyl alcohol. This solution is applied to the core using an air spray system.

Next, the enteric coating materials (HP 55® and Myvacet 9–45®) are mixed and sprayed onto the surface of the membrane by use of an air spray system.

Publications
1. Hardy, J. G., et al, J. Pharm. Pharmacol. 37:874–877 (1985).
2. Dew, M. J., et al, Clin. Pharmacol. 14: 405–408 (1982).
3. Saffran, M., et al, Science 233: 1081–1084 (1988).
4. Ueda, Y., et al, U.S. Pat. No. 4,871,549 (1989).
5. Iamartino, P., et al, U.S. Pat. No. 5,171,580 (1992).
6. Phuapradit, W., et al, Drug Development and Industrial Pharmacy, 21: 955–963 (1995).
7. Roberts, N. A., et al, Science 248: 358 (1990)
8. Overton, H. A., et al, Virology 179: 508 (1990)
9. Tucker, T. J, et al, J. Med. Chem. 35: 2525 (1992)
10. Phylip, L. H., et al, FEBS Letters, 314: 449 (1992)

What is claimed is:
1. A drug delivery system comprising:
   a) a core containing a therapeutically effective amount of a biologically-active compound and a swelling agent said swelling agent being present in an amount of from about 5 to about 50% w/w of the core;
   b) a semi-permeable polymer membrane encasing the core which allows water influx but prevents outward diffusion of the biologically active compound, said membrane including a plasticizer, which plasticizer is present in an amount of from about 10 to about 30% w/w of the membrane, wherein the membrane has a percent elongation of from about 2 to about 3.5%; and
   c) an outer enteric coating encasing the membrane which coating dissolves at or above about pH 5.5.
2. The system of claim 1, wherein the swelling agent is selected from the group consisting of croscarmellose sodium, modified starch, sodium carboxymethylcellulose, cross-linked polyvinyl pyrrolidone, mannitol and combinations thereof.
3. The system of claim 2, wherein the swelling agent is a combination of croscarmellose sodium and mannitol.
4. The system of claim 1, wherein the swelling agent is from about 10% to about 30% w/w of the core.
5. The system of claim 1, wherein the polymer material is selected from the group consisting of ethylcellulose, cellulose acetate, cellulose triacetate, cellulose tributyrate and polyvinyl chloride, and wherein the plasticizer is dibutyl sebecate.
6. The system of claim 5, wherein the polymer material is ethylcellulose.
7. The system of claim 1, wherein the plasticizer represents about 75% w/w of the membrane.
8. The system of claim 1, wherein the membrane has
   (i) a tensile strength from about 1000 to about 3500 psi;
   (ii) a modulus of elasticity of from about 95 to about 150 ksi;
   (iii) and a thickness of from about 50 $\mu$m to about 400 $\mu$m.
9. The system of claim 1, wherein the plasticizer is selected from the group consisting of dibutyl sebecate; acetylated monoglycerides, dibutyl phthalate, diethyl phthalate, and medium chain triglycerides.
10. The system of claim 9, wherein the plasticizer is dibutyl sebecate.
11. The system of claim 1, wherein said biologically-active compound is 2-hydroxy-4-[5-(2,3-dihydroxyphenyl)-pentyloxy]-3-propyl benzoic acid.
12. The system of claim 1, wherein said biologically-active compound is N-tert.butyldecahydro-2-2(R)-hydroxy-4-phenyl-3(S)-N-2-quinolylcarbonyl-L-asparaginyl aminobutyl-4aS, 8aS isoquinoline-3(S)-carboxamide.
13. The system of claim 3, wherein:
   (i) the croscarmellose sodium represents from about 6 to about 7% w/w of the core;
   (ii) the mannitol represents about 20% w/w of the core;
   (iii) the semi-permeable membrane comprises ethylcellulose containing dibutyl sebecate which dibutyl sebecate is present at about 15% w/w of the membrane; and
   (iv) the outer entric coating has a thickness of about 300 $\mu$m and comprises hydroxypropyl methyl-cellulose phthalate containing distilled acetylated monoglyceride, which monoglyceride is present at about 10% w/w of the enteric coating.
14. The system of claim 1, wherein the polymer material is selected from the group consisting of ethylcellulose, cellulose acetate, cellulose triacetate, cellulose tributyrate, and polyvinyl chloride.

* * * * *